US009826919B2

(12) United States Patent
Amiot et al.

(10) Patent No.: US 9,826,919 B2
(45) Date of Patent: Nov. 28, 2017

(54) CONSTRUCTION OF A NON-IMAGED VIEW OF AN OBJECT USING ACQUIRED IMAGES

(75) Inventors: Louis-Philippe Amiot, Hampstead (CA); François Poulin, Brossard (CA); Mélanie Chassé, Deux-Montagnes (CA)

(73) Assignee: ORTHOSOFT, INC., Montreal (CA)

( * ) Notice: Subject to any disclaimer, the term of this patent is extended or adjusted under 35 U.S.C. 154(b) by 1362 days.

(21) Appl. No.: 12/241,724

(22) Filed: Sep. 30, 2008

(65) Prior Publication Data

US 2009/0087052 A1 Apr. 2, 2009

Related U.S. Application Data

(60) Provisional application No. 60/960,476, filed on Oct. 1, 2007.

(51) Int. Cl.
*G06K 9/00* (2006.01)
*A61B 5/107* (2006.01)
(Continued)

(52) U.S. Cl.
CPC ............ *A61B 5/1075* (2013.01); *A61B 6/463* (2013.01); *A61B 6/465* (2013.01); *A61B 34/20* (2016.02);
(Continued)

(58) Field of Classification Search
USPC ........ 600/407, 425, 426, 594; 382/132, 294, 382/295
See application file for complete search history.

(56) References Cited

U.S. PATENT DOCUMENTS

| 5,227,969 A | 7/1993 | Waggener et al. |
| 5,787,889 A | 8/1998 | Edwards et al. |

(Continued)

FOREIGN PATENT DOCUMENTS

| CA | 2202052 | 4/1996 |
| FR | 2 790 125 | 8/2005 |

(Continued)

OTHER PUBLICATIONS

International Search Report, PCT/CA2008/001730, dated Dec. 11, 2008.

(Continued)

*Primary Examiner* — Joseph M Santos Rodriguez
(74) *Attorney, Agent, or Firm* — Norton Rose Fulbright Canada LLP (57) ABSTRACT

There is described a method and a system for generating a non-imaged plane view of an anatomical part for assisting a surgery. A model of the anatomical part is provided, comprising features and dimension parameters. A first plane view of the anatomical part is obtained. Features are identified in the first plane view. The dimension parameters are measured from the features identified. The model is displayed in the non-imaged plane view such that the model is dimensioned with the measured dimension parameters. A position and orientation of a surgical object is then tracked relative to the anatomical part while a user navigates the surgical object in space and a representation of the surgical object to be overlaid in register on at least one the first plane view and/or the non-imaged view is generated.

16 Claims, 12 Drawing Sheets

(51) Int. Cl.
  *A61B 6/00* (2006.01)
  *A61B 34/20* (2016.01)
  *A61B 5/055* (2006.01)
  *A61B 5/00* (2006.01)
  *A61B 6/12* (2006.01)
  *G06F 19/00* (2011.01)
  *A61B 34/10* (2016.01)

(52) U.S. Cl.
  CPC .......... *G06F 19/3437* (2013.01); *A61B 5/055* (2013.01); *A61B 5/4504* (2013.01); *A61B 5/4561* (2013.01); *A61B 6/12* (2013.01); *A61B 2034/102* (2016.02); *A61B 2034/105* (2016.02); *G06F 19/321* (2013.01); *G06F 19/3481* (2013.01)

(56) References Cited

U.S. PATENT DOCUMENTS

| | | | |
|---|---|---|---|
| 6,491,429 B1 * | 12/2002 | Suhm | 378/205 |
| 6,603,868 B1 * | 8/2003 | Ludwig et al. | 382/128 |
| 6,814,489 B2 | 11/2004 | Jensen et al. | |
| 6,920,240 B2 | 7/2005 | Rodet et al. | |
| 6,980,922 B2 * | 12/2005 | Henderson et al. | 702/152 |
| 7,269,241 B2 | 9/2007 | Siltanen et al. | |
| 2002/0082492 A1 * | 6/2002 | Grzeszczuk | 600/407 |
| 2003/0185346 A1 | 10/2003 | Vilsmeier | |
| 2004/0171922 A1 | 9/2004 | Rouet et al. | |
| 2005/0004451 A1 | 1/2005 | Vilsmeier et al. | |
| 2005/0008219 A1 * | 1/2005 | Pomero et al. | 382/154 |
| 2005/0018901 A1 * | 1/2005 | Kaufmann et al. | 382/154 |
| 2005/0100203 A1 | 5/2005 | Fujisawa | |
| 2005/0220264 A1 | 10/2005 | Homegger | |
| 2005/0245807 A1 | 11/2005 | Boese et al. | |
| 2006/0079759 A1 | 4/2006 | Vaillant et al. | |
| 2006/0100507 A1 | 5/2006 | Mertelmeier | |
| 2006/0262894 A1 | 11/2006 | Bernhardt et al. | |
| 2007/0073195 A1 * | 3/2007 | Chen | 600/594 |
| 2007/0110210 A1 | 5/2007 | Nishide et al. | |
| 2007/0116334 A1 | 5/2007 | Fidrich et al. | |
| 2008/0039711 A1 | 2/2008 | Feilkas et al. | |
| 2008/0049014 A1 | 2/2008 | Haimerl et al. | |

FOREIGN PATENT DOCUMENTS

| | | |
|---|---|---|
| WO | WO2006063141 A2 | 6/2006 |
| WO | WO-2006/131646 | 12/2006 |
| WO | WO-2007/069144 | 6/2007 |
| WO | WO20070911464 A1 | 8/2007 |

OTHER PUBLICATIONS

Wicker, Ryan, Tedla, Buz, *Automatic Determination of Pedicle Screw Size, Length, and Trajectory from Patient Data*, proceedings of the 26th Annual International Conference of the IEEE EMBS, San Francisco, CA, Sep. 1-5, 2004.

* cited by examiner

CONSTRUCTION OF A NON-IMAGED VIEW OF AN OBJECT USING ACQUIRED IMAGES

CROSS-REFERENCE TO RELATED APPLICATIONS

This application claims priority under 35 USC§119(e) of U.S. Provisional Patent Application No. 60/960,476 filed Oct. 1, 2007, the specification of which is hereby incorporated by reference.

TECHNICAL FIELD

The present application relates to the field of imaging devices and more specifically, to the visualization of different plane views of an object. Amongst other uses, the imaging devices are part of computer-assisted surgery systems.

BACKGROUND

There are a variety of computer-assisted surgery systems that exist for assisting a surgeon during a surgery. Such systems allow the surgeon to view the anatomy of a patient during surgery in order to be guided throughout the procedure. Surgical navigation using medical imaging is based on displaying, in real-time, instruments and patient anatomy to allow visualization of the complete surgical field. Patient anatomy can be obtained from a number of sources, such as CT-scan, digitization, fluoroscopy, Magnetic Resonance Imaging (MRI), and other such known technologies.

There are at least three body planes that each provides a different view of the anatomy. These body planes are generally referred to as the coronal or antero-posterior plane, sagittal or lateral plane, and transverse or axial plane. Each imaging source is designed to generate certain views of the body. For example, a CT-scan will take multiple slices of the anatomy, thereby providing axial planes throughout. A fluoroscope can take antero-posterior plane views and sagittal plane views.

In certain instances, a given view will provide information that is more useful to the surgeon during navigation than another view. However, a single type of imaging device may not necessarily be capable of generating all three views. The missing view(s) is(are) therefore not available or only available using another imaging device.

SUMMARY

It is an aim of the present application to provide a system and a method that address issues associated with the prior art.

There are provided a system and a method which allow obtaining a different plane view of an object from plane view images acquired on the object using an imaging device.

In accordance with an embodiment, there is provided herewith a method for generating a non-imaged plane view of an anatomical part in computer-assisted surgery, the method comprising: providing a model of the anatomical part comprising features and dimension parameters related to said features; obtaining at least a first plane view of the anatomical part; identifying said features in said at least first plane view; measuring values of said dimension parameters from said features identified in said at least first plane view; displaying, in said non-imaged plane view, said model dimensioned with said dimension parameters adjusted to said values; tracking a position and orientation of a surgical object relative to said anatomical part while a user manipulates said surgical object in space; and generating a representation of said surgical object to be overlaid in register on said non-imaged view, using the tracked position and orientation.

In accordance with another embodiment, there is provided herewith a computer-assisted surgery system for generating a non-imaged plane view of an anatomical part for assisting a surgery, the system comprising: an imaging acquisition device having a first axis for obtaining a first plane view of the anatomical part; an image generating device providing a model of said anatomical part comprising: a feature identification unit for identifying features of said anatomical part in at least said first plane view; a parameter measuring unit for measuring values of dimension parameters from said features identified; and a model dimensioning unit for dimensioning said model of said anatomical part with said dimension parameters adjusted to said values; a display device for displaying, in said non-imaged plane view, the model as dimensioned; and a navigation processing device for generating a representation of a surgical object to be overlaid in register on at least said non-imaged view, using a tracked position and orientation of said surgical object relative to said anatomical part, to provide visual feedback on at least said non-imaged view while said surgical object is manipulated.

While the following detailed description concerns the generation of an axial plane view using antero-posterior and sagittal plane views, it should be understood that any two orthogonal views may be used to generate a third view in accordance with the methods and systems described herein.

It is also noted that a human body is used in the following description for exemplary purposes only. Other types of body, or other three dimensional objects, can be imaged and the images treated as presented herein. It should be understood that while the orthogonal plane views described are associated to a body, any orthogonal plane view associated to a three-dimensional object can be used.

In addition, while the method will be described using x-ray or fluoroscopic imaging devices, it should be understood that other types of imaging devices, such as Positron Emission Tomography (PET), Computed Tomography scan (CT-scan) and Magnetic Resonance Imaging (MRI), may be used as well. The type of surgery is not limited to spinal surgery and the implant is not limited to a pedicle screw.

BRIEF DESCRIPTION OF THE DRAWINGS

It will be noted that throughout the appended drawings, like features are identified by like reference numerals.

DETAILED DESCRIPTION

Figure 1:
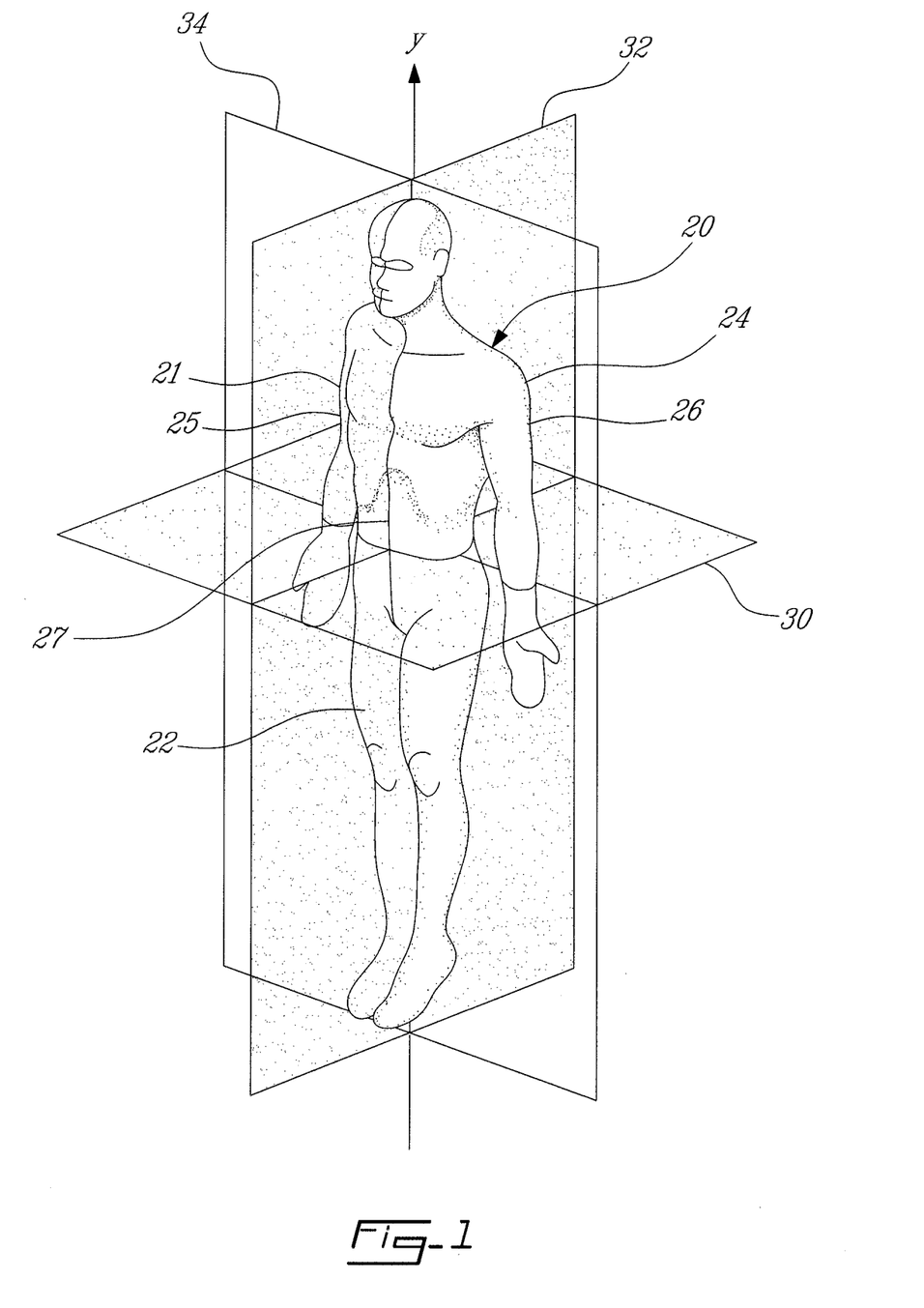
FIG. 1 is a schematic illustrating a body and its three anatomical planes.

FIG. 1 illustrates the three anatomical planes of the human body 20. The body 20 is defined as having an upper section 21, a lower section 22, a left side 24, a right side 25, a back 26 and a front 27.

The axial plane 30 (also known as the transverse plane) is a transverse cut of the body 20, between the upper section 21 and the lower section 22. The axial plane 30 is generally normal to a cranial-caudal axis Y (i.e., body axis or vertical axis).

The sagittal plane 32 (also referred to as the lateral plane) is a lateral cut of the body 20, between its left and right sides 24 and 25, and parallel to the cranial-caudal axis Y. The sagittal plane 32 is also orthogonal to the axial plane 30.

The antero-posterior plane 34 (also known as the frontal plane of the coronal plane) is a frontal cut of the body 20, between the back 26 and the front 27, parallel to the cranial-caudal axis Y. The antero-posterior plane 34 is also orthogonal to the sagittal plane 32 and to the axial plane 30.

Images taken from each one of these planes 30, 32 and 34, provide different information on the anatomy of the body 20.

Figure 2:
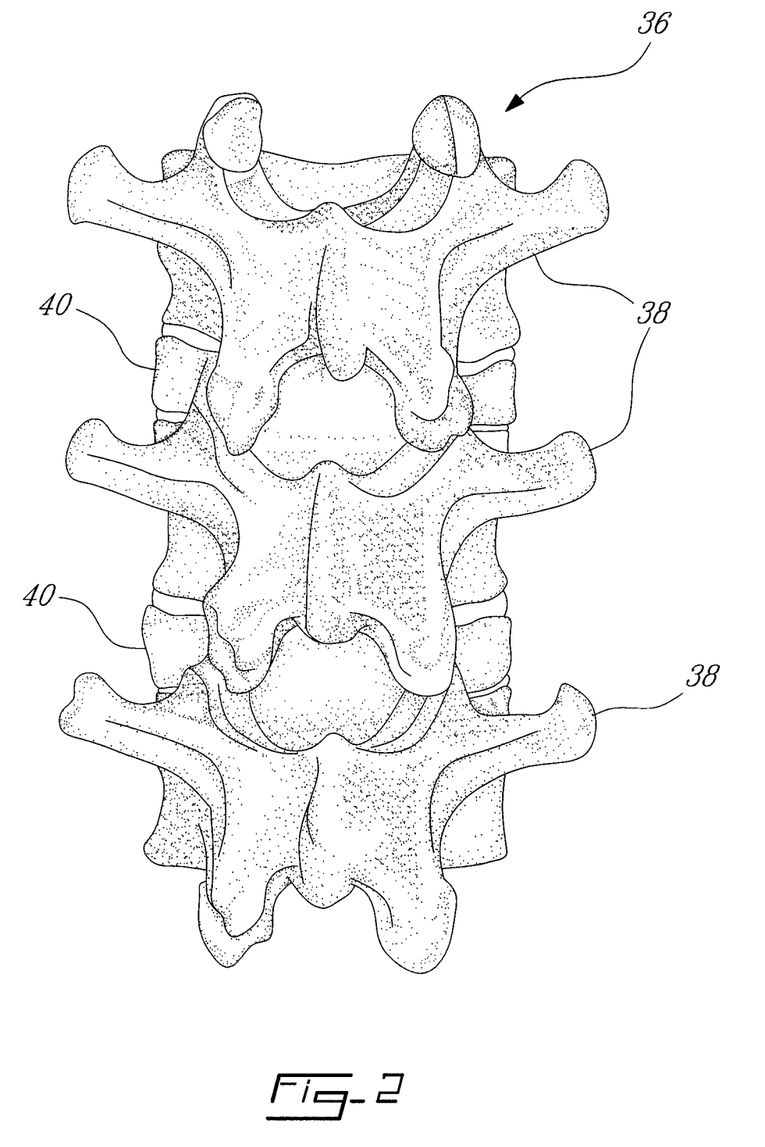
FIG. 2 is a back elevation view of a portion of a spinal column of the body of FIG. 1.

FIG. 2 is a back view of a portion of the spinal column 36. The spinal column (or vertebral column) 36 extends from the skull to the pelvis and is made up of multiple individual bones called vertebrae 38. The vertebrae 38 are stacked on top of each other interleaved with discs 40.

Figure 3A:
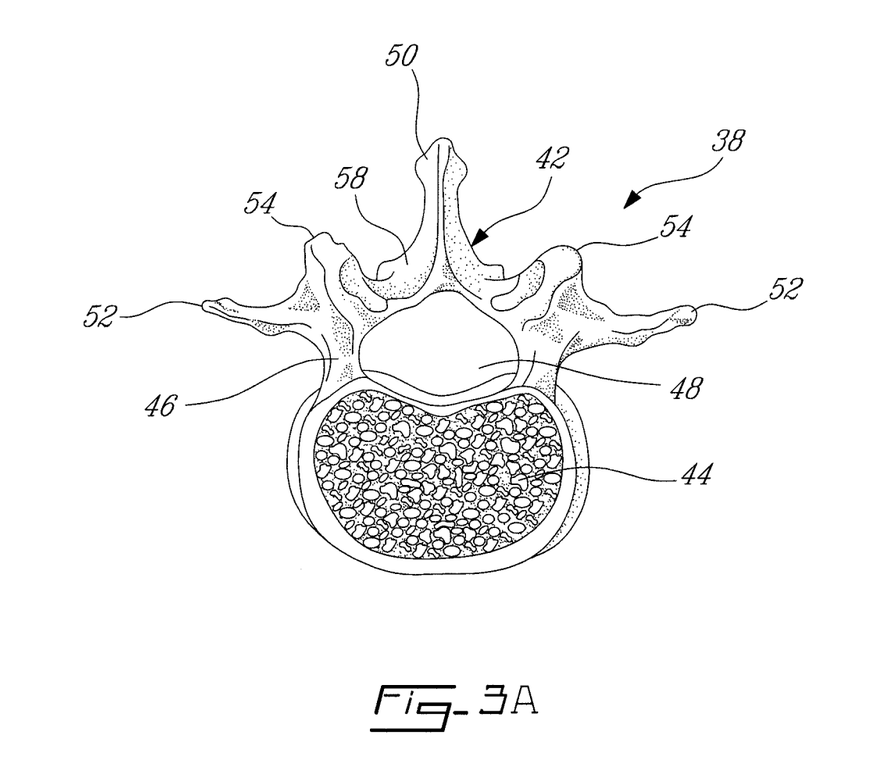
FIG. 3A is an axial plane view of a normal lumbar vertebra of the body of FIG. 1.
Figure 3B:
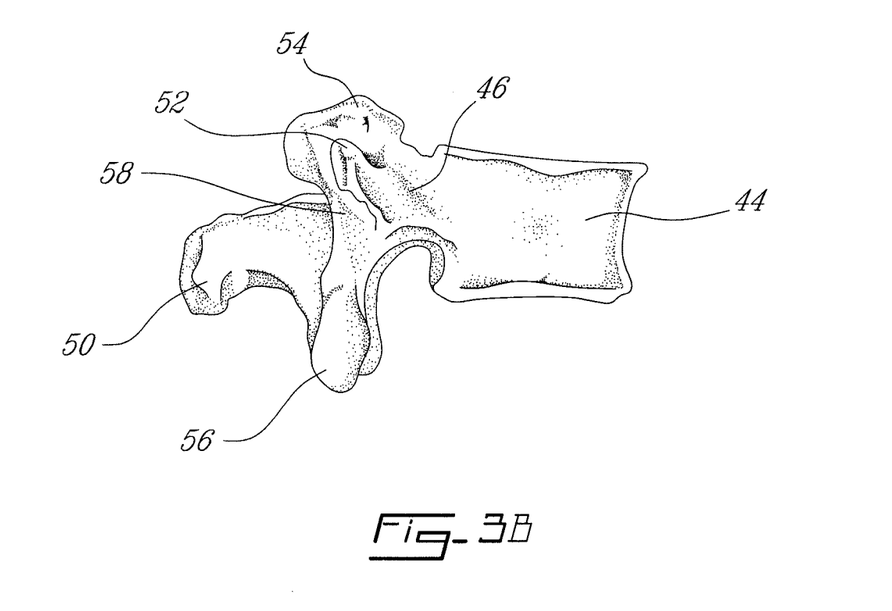
FIG. 3B is a side elevation view of the normal lumbar vertebra of FIG. 3A.

FIGS. 3A and 3B are respectively a top view and a side view of a normal lumbar vertebra 38. The vertebra 38 has a back portion 42 and a front portion, called the vertebral body 44, linked by two pedicles 46. The back portion 42, the vertebral body 44 and the pedicles 46 define a spinal canal 48, and through which the spinal cord (not shown) passes. The back portion 42 has a spinous process 50 protruding toward the back, a transverse process 52 protruding toward each side, two superior articular facets 54 protruding upward and two inferior articular facets 56 protruding downward (FIG. 3B). The spinous process 50, the transverse processes 52, the superior articular facets 54 and the inferior articular facets 56 are linked by a lamina 58.

A method and a system for generating a non-imaged plane view of an object, a vertebra in this embodiment, are described herein with reference to FIGS. 4 to 12.

Figure 4:
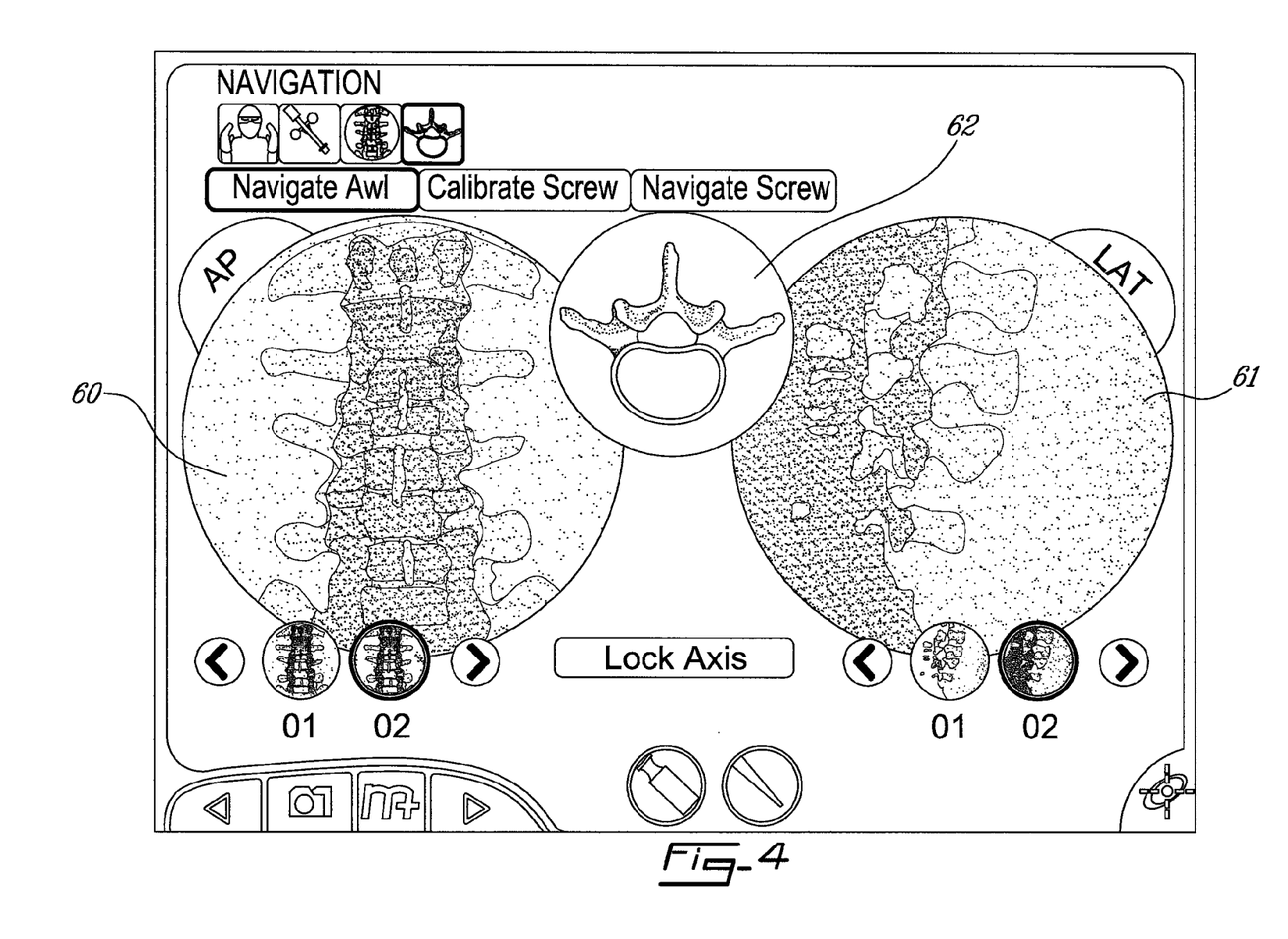
FIG. 4 is schematic view illustrating a screenshot of a graphical user interface (GUI) of a computer-assisted surgery system, showing an antero-posterior imaged view and a sagittal imaged view of a spine of the body of FIG. 1, and an axial view of a vertebra of the spine, as obtained from the imaged views, in accordance with an example embodiment.

FIG. 4 shows a screenshot of a graphical user interface (GUI) as displayed on a display device of a computer-assisted surgery (CAS) system. Two imaged, i.e. acquisition-obtained, plane views 60, 61 are represented thereon. These plane views 60, 61 are acquired using a fluoroscopic apparatus. As discussed hereinbelow, the CAS system also allows the tracking and the reproduction on the display device of surgical objects, such as a surgical tool, overlaid on these two plane views 60, 61, as a surgeon places a pedicular screw into a given vertebra for example.

The imaged plane view 60 located on the left side is a fluoroscopic image of the spine acquired along the antero-posterior plane 34 (see FIG. 1). The imaged plane view 61 located on the right side is a fluoroscopic image of the spine taken along the sagittal plane 32 (see FIG. 1). An additional plane view, i.e. a non-imaged plane view 62, is also shown positioned centrally between the antero-posterior plane view image 60 and the sagittal plane view image 61. The plane view shown by non-imaged plane view 62 represents a plane view of the spine taken along the axial plane 30 (see in FIG. 1). The plane view 62 is non-imaged in that it is not obtained from an imaging acquisition but is rather generated from the antero-posterior plane view image 60 and the sagittal plane view image 61 as described hereinbelow. The non-imaged plane view 62 is actually generated from a model of a typical vertebra which is defined by a typical shape and a combination of features and dimension parameters. Dimensions of the model are adjusted according to measurements of the dimension parameters performed on the antero-posterior plane view image 60 and the sagittal plane view image 61. It is pointed out that the configuration of the GUI of FIG. 4 is shown as an example. Other configurations may be displayed, with the plane image 62 to the right-hand side or left-hand side, or without the image 60 and/or 61.

Figure 5:
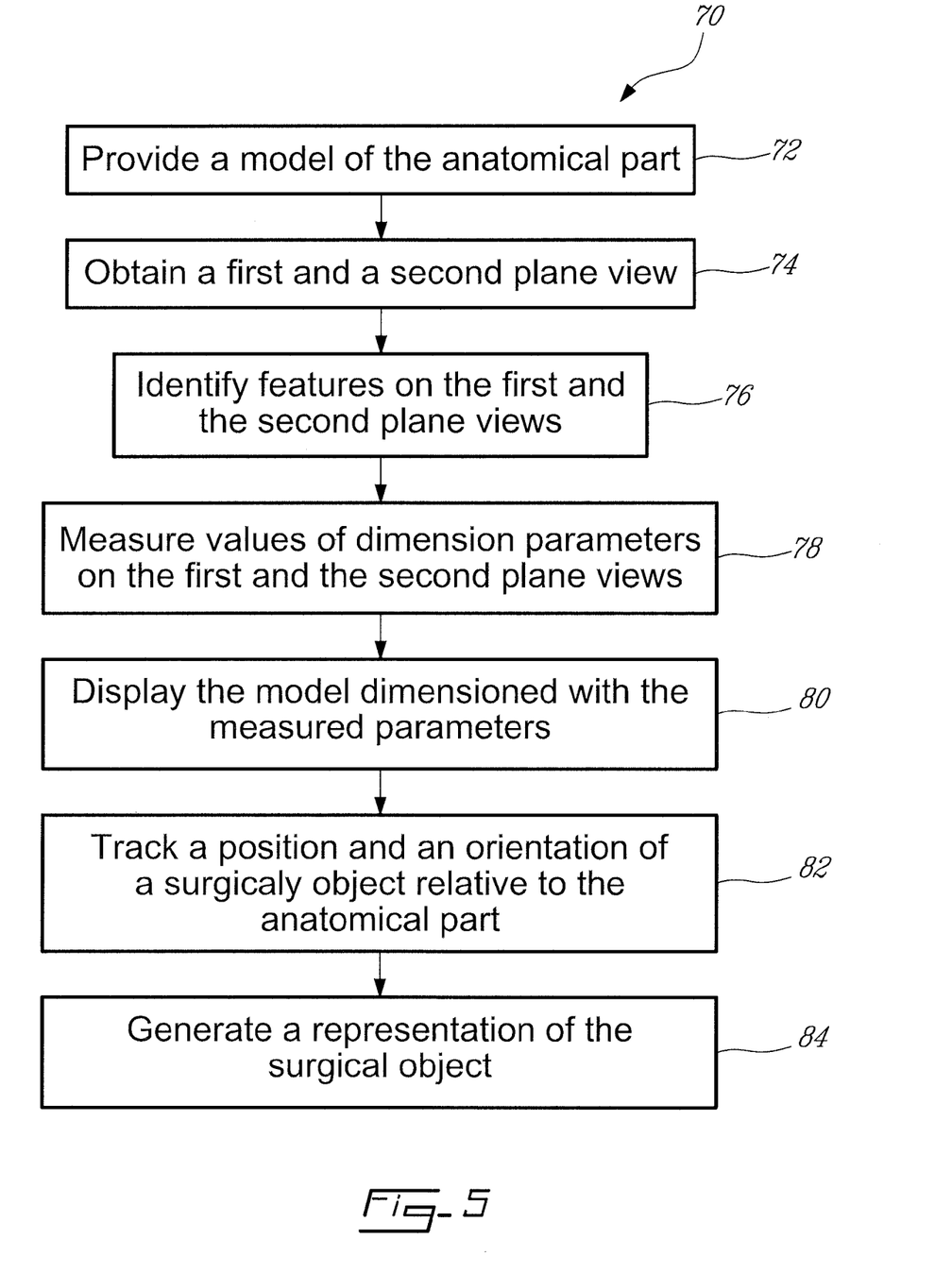
FIG. 5 is a flow chart of a method for generating a non-imaged plane view of an object, in accordance with an example embodiment.

FIG. 5 illustrates the steps of a method 70 for generating a non-imaged plane view of an anatomical part, such as the non-imaged plane view 62 of FIG. 4, from at least one plane view, such as plane view images 60 and 61 of FIG. 4.

In step 72, a model of the anatomical part, such as a model of a typical vertebra or other bone, is provided. The model generally defines the shape of the anatomical part in general with representative features that are typical to the shape of the anatomical part. The dimensions of the general shape are to be adjusted according to dimension parameters related to the features and determined from the plane view images 60 and 61. In the case of a vertebra, the general shape corresponds to the one shown in FIGS. 3A and 3B. As will be detailed hereinbelow, the features are typically defined by contours of the anatomical part, such as the contours of some of the following elements in the case of a vertebra: the spinous process 50, the transverse processes 52, the superior articular facets 54, the inferior articular facets 56, the pedicles 46 and the vertebral body 44 (see FIGS. 3A and 3B). Dimension parameters may comprise the distance between the various contours. An example of features and dimension parameters for the specific case of a vertebra are given hereinbelow with reference to FIG. 6A.

In step 74, a first plane view and, optionally, a second plane view of the anatomical part are obtained using an imaging device. The first and the second plane views are typically orthogonal from one another. The first and the second plane views of the anatomical part can typically be any two of an antero-posterior plane view, a sagittal plane view and an axial plane view. In the specific embodiment described herein, the first plane view consists of the antero-posterior plane view image 60 and the second plane view consists of the sagittal plane view image 61. Also in the specific embodiment described herein, the first and second plane views are acquired using the same imaging device. Two different imaging devices may also be used to obtain the two orthogonal plane views.

In step 76, features of the anatomical part are identified on the first plane view and also typically on the second plane view. As will be detailed hereinbelow, the features are typically defined by contours of the anatomical part as extracted from the first and the second plane views.

In step 78, values of the dimension parameters are measured on the first plane view and also typically on the second plane view, from the features identified in step 76. The distance between various features of the vertebra may be measured from the antero-posterior plane view image 60 and the sagittal plane view image 61. In the specific embodiment described herein, the dimension parameters are the distances $d_1$, $d_2$, $d_3$ and $d_4$ as described hereinbelow with reference to FIG. 6A.

In step 80, the model of the anatomical part is displayed in the non-imaged plane view, as dimensioned according to the values measured in step 78. Accordingly, the model is scaled to correspond to the values of the dimension parameters measured in step 78. In the specific embodiment described herein, the model of the vertebrae is displayed in the non-imaged plane view 62.

Further to displaying the model of the anatomical part to generate the non-imaged plane view, all of the three views, i.e. the first and the second plane views and the non-imaged plane view, can be displayed on the display device (see FIG. 4 for example).

In step 82, the position and the orientation of a surgical object, such as a surgical tool, are tracked relative to the anatomical part while the user manipulates the surgical object in space. As explained below, this is typically made using tracking modules installed on the anatomical part and on the surgical object.

In step 84, a representation of the surgical object to be overlaid in register on the first plane view, the second plane view and/or the non-imaged plane view is generated using the tracked positions and orientations of the surgical object relative to the anatomical part.

A specific example of steps 76 and 78 of the method illustrated in FIG. 5 is now described with reference to the images 60 and 61, and the non-imaged plane view 62 of FIG. 4 and to FIGS. 6A-6E and 7A-7C. It is pointed out that FIGS. 6A-6E and 7A-7C are schematic representations of a vertebra, and are provided for illustrative purposes only. The following is used to identify the features of the vertebra in the antero-posterior plane view 60 and the saggital plane view 61.

Figure 6A:
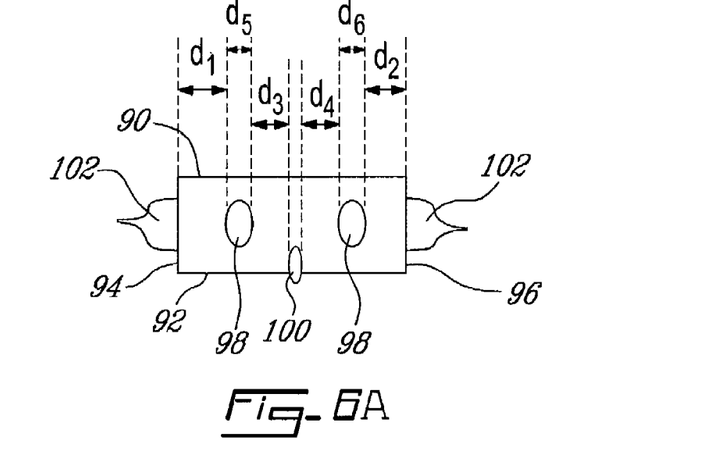
FIG. 6A is a schematic view illustrating a typical contour-defined vertebra as obtained from the antero-posterior plane imaged view of FIG. 4.

FIG. 6A illustrates the model of a vertebra as seen from the antero-posterior plane view 60 and defined by contours. The algorithm identifies features of a given target vertebra, which are defined as different contours of the vertebra. The contours identified are: the upper vertebral body contour 90, the lower vertebral body contour 92, the left-side vertebral body contour 94, and the right-side vertebral body contour 96, as well as the pedicles contours 98, the spinous process contour 100, and the transverse processes contours 102. Each of these contours respectively represent the following elements as represented in FIGS. 3A and 3B: the vertebral body 44 from the upper side, lower side, left and right sides, each one of the pedicles 46, the spinous process 50 and the transverse processes 52.

Distances $d_1$, $d_2$, $d_3$, $d_4$, $d_5$ and $d_6$ define dimension parameters of the vertebra model, according to the specific example described herein. Distances $d_1$ and $d_2$ respectively define a distance between the left-side vertebral body contour 94 and the closest pedicle contour 98; and between the right-side vertebral body contour 96 and the closest pedicle contour 98. Distances $d_3$ and $d_4$ respectively define a distance between the spinous process contour 100 and each one of the pedicle contours 98. Distances $d_5$ and $d_6$ respectively define a width of the left-side and right-side pedicle contours 98.

The contour image of FIG. 6A is obtained if the pedicles 46 (see FIGS. 3A and 3B) are placed substantially parallel to the imaging device's axis when acquiring the image 60 in the antero-posterior plane. In this case, the distances $d_1$ and $d_2$ are substantially equivalent or only vary slightly with one another.

Figure 6B:
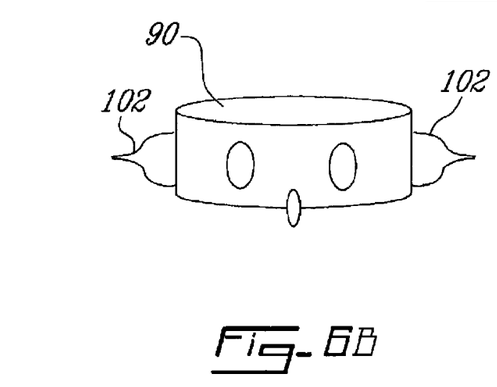
FIG. 6B is a schematic view illustrating a typical downward-tilted contour-defined vertebra as obtained from the antero-posterior plane imaged view of FIG. 4.

If the image 60 is taken such that the vertebra is tilted upwards, the contour image of FIG. 6B results. An ellipse is formed along the upper vertebral body contour 90.

Figure 6C:
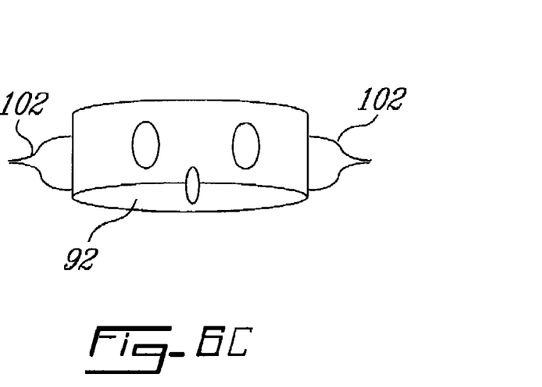
FIG. 6C is a schematic view illustrating an typical upward-tilted contour-defined vertebra as obtained from the antero-posterior plane imaged view of FIG. 4.

If the image 60 is taken such that the vertebra is tilted downwards, the contour image of FIG. 6C results. An ellipse is formed along the lower vertebral body contour 92.

Figure 6D:
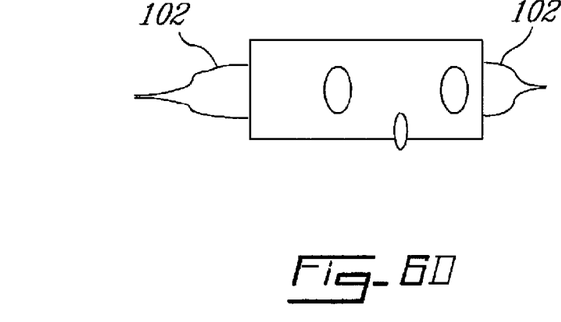
FIG. 6D is a schematic view illustrating a typical right-side-tilted contour-defined vertebra as obtained from the antero-posterior plane imaged view of FIG. 4.
Figure 6E:
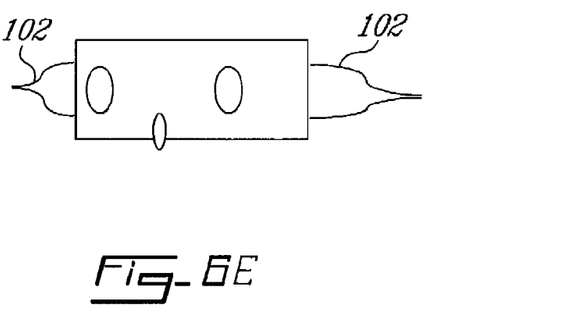
FIG. 6E is a schematic view illustrating a typical left-side-tilted contour-defined vertebra as obtained from the antero-posterior plane imaged view of FIG. 4.

If the image 60 is taken such that the vertebra is tilted toward the right or the left, the contour images of FIGS. 6D and 6E respectively result. In such cases, the sizes of the contours 102 representing the transverse processes 52 (see FIGS. 3A and 3B) are disproportional with one another and the distances $d_1$ and $d_2$ are not substantially equivalent in comparison with those of FIG. 6A. The distances $d_3$ and $d_4$ are also not substantially equivalent to one another.

Hence, when the image 60 is obtained in step 74, the imaging device and/or the body are oriented with respect to one another such that the distance pairs $d_1$, $d_2$; $d_3$, $d_4$; and/or $d_5$, $d_6$ are substantially matched. However, the distance pairs do not need to be exactly matched to one another, in order to account for natural incongruence that may exist based on known anatomical information.

Figure 7A:
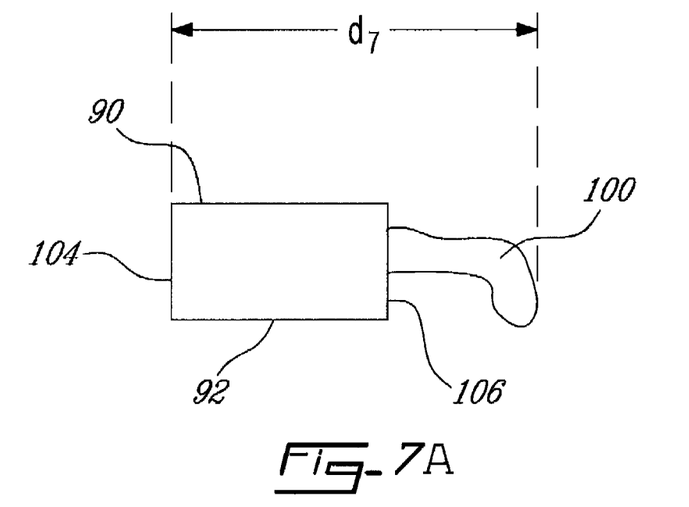
FIG. 7A is a schematic view illustrating a typical contour-defined vertebra as obtained from the sagittal plane imaged view of FIG. 4.

Still in accordance with a specific example of the above method, a similar process is performed on the sagittal plane view 61.

FIG. 7A illustrates the model of a vertebra as seen from the sagittal plane view 61 and defined by contours. The upper and lower vertebral body contours 90 and 92 are identified, as well as the front vertebral body contour 104, the back vertebral body contour 106, and the spinous process contour 100. A distance $d_7$ defines another dimension parameter of the vertebra model, according to the specific example described herein. The distance $d_7$ defines a distance between the front vertebral body contour 104 and the back end of the spinous process contour 100.

Figure 7B:
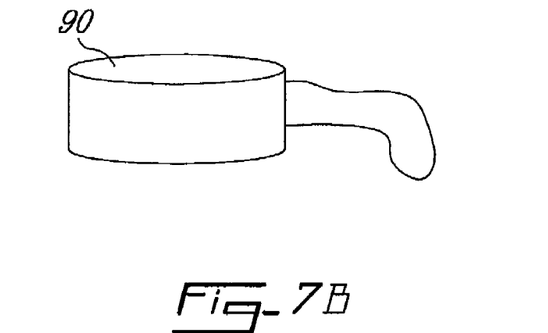
FIG. 7B is a schematic view illustrating a typical upward-tilted contour-defined vertebra as obtained from the sagittal plane imaged view of FIG. 4.
Figure 7C:
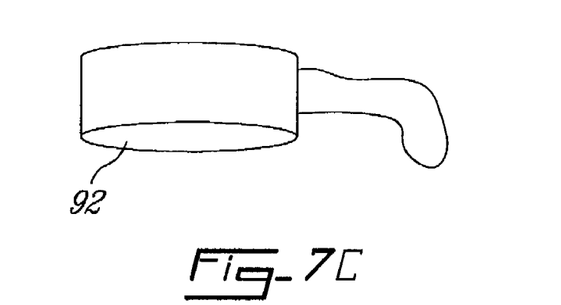
FIG. 7C is a schematic view illustrating a typical downward-tilted contour-defined vertebra as obtained from the sagittal plane imaged view of FIG. 4.

As illustrated in FIGS. 7B and 7C, respectively, if the target vertebra in the sagittal plane view 61 is tilted upwards or downwards, ellipses are formed along the upper and lower vertebral body contours 90 and 92, which may create distortions in the contour data.

Hence, when the sagittal plane view 61 is obtained in step 74 of FIG. 5, the imaging device and the body are oriented with respect to each other such that ellipses in the vertebral body contour 90 and 92 are eliminated as much as possible.

After identifying the contours 90, 92, 94, 96, 98, 100, 102, 104 and 106 on the antero-posterior plane view 60 and on the sagittal plane view 61, at least some of the dimension parameters $d_1$, $d_2$, $d_3$, $d_4$, $d_5$, $d_6$ and $d_7$ are measured on the plane views 60, 61. The model of the vertebra may then be dimensioned according to selected ones of $d_1$, $d_2$, $d_3$, $d_4$, $d_5$, $d_6$ and $d_7$ and displayed in the non-imaged plane view 62.

An additional step may be used after the contours are identified, to determine whether each one of the first and second plane views is acceptable for further processing. This step may be performed manually by a surgeon using his best judgment, with the help of a computer or not. Values of the dimension parameters, such as $d_1$, $d_2$, $d_3$ and $d_4$, measured from the contours may also be compared using a computer algorithm. The algorithm thresholds the measured values and determines if they are within an acceptable margin, indicating whether the plane views acquired are in proper alignment with the anatomical part for further processing towards the generation of the non-imaged plane view. The result of the comparison is then optionally used to obtain correct views by reorienting the imaging device used to obtain the plane view with respect to the anatomical part. Moreover, the shape of the vertebra parts on the plane views may be used by the operator to determine whether the alignment was proper between the imaging device and the patient. For instance, a deformed shape of a pedicle may be judged by the operator as a misalignment between the imaging device and the patient.

Figure 8:
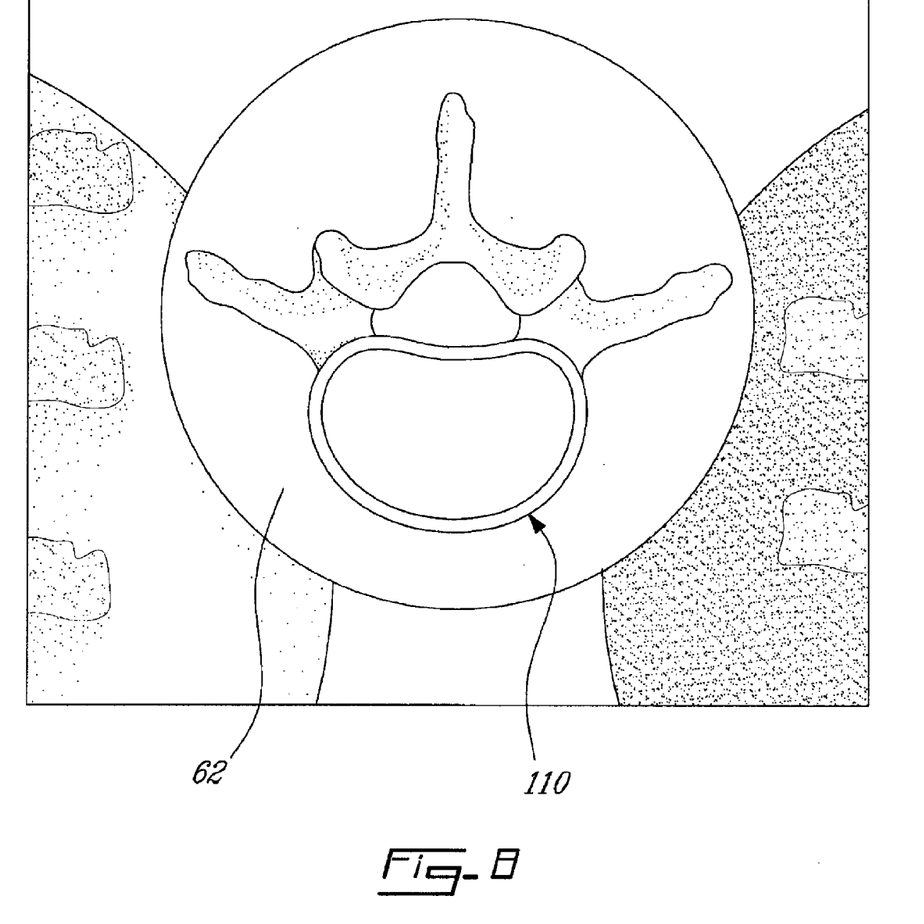
FIG. 8 is an enlarged view of the axial plane view of the vertebra of FIG. 4.

FIG. 8 shows an enlarged view of the axial plane view 62 generated using the antero-posterior plane view 60 and the sagittal plane view 61. The target vertebra 110 is displayed. The displayed vertebra 110 is dimensioned in accordance with the measurements taken from the antero-posterior view ($d_1$, $d_2$, $d_3$, and $d_4$) and the measurements taken from the sagittal view ($d_5$). A standard model of the vertebra is then used and proportioned according to the dimension parameters $d_1$, $d_2$, $d_3$, $d_4$ and $d_5$. The non-imaged axial view 62 of the target vertebra is thus made to correspond to the actual measurements obtained from the imaged plane views 60, 61.

Figure 9:
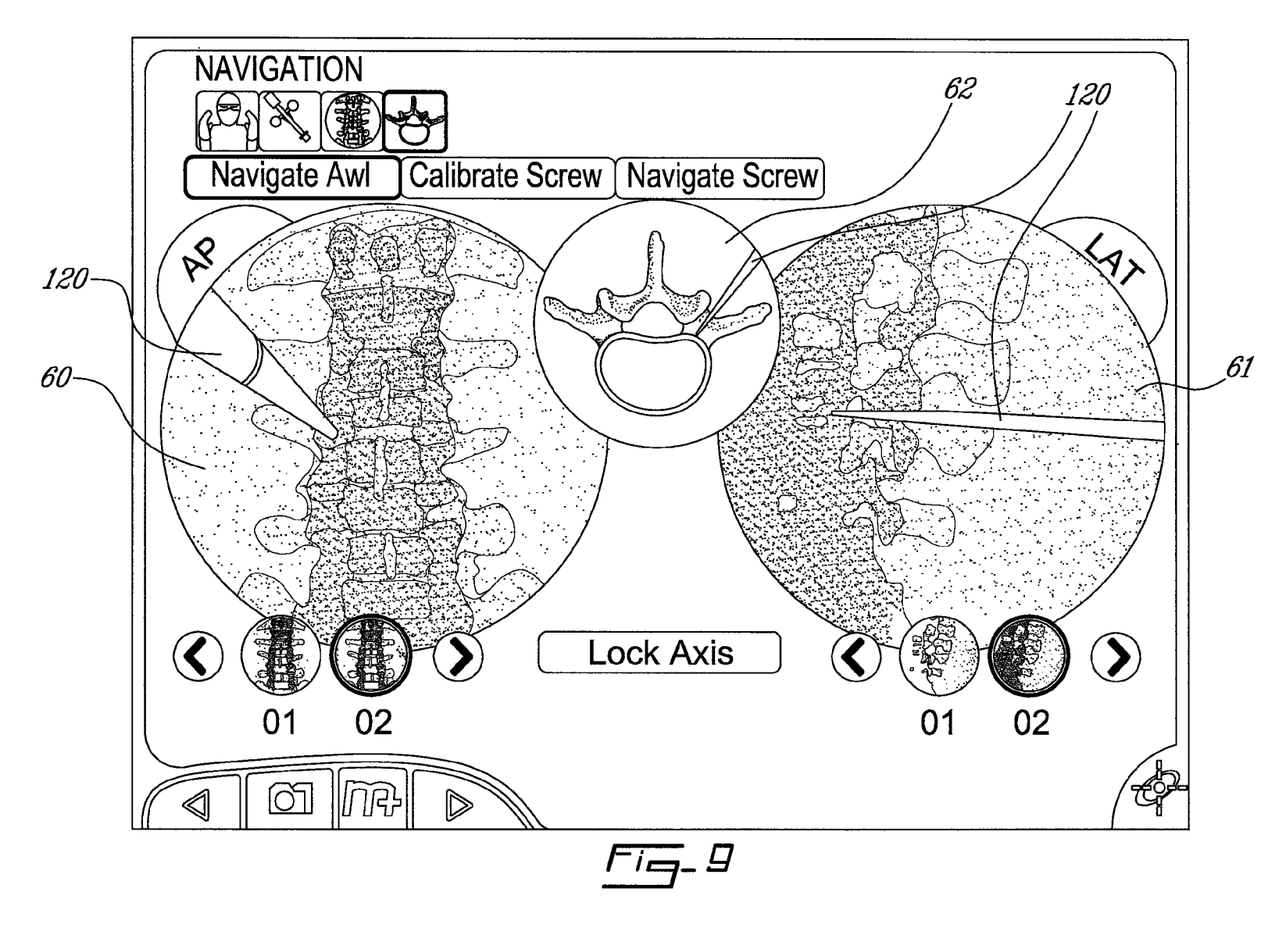
FIG. 9 is schematic illustrating a screenshot of the GUI of FIG. 4, wherein an awl is shown in register with the vertebra.

FIG. 9 shows a screenshot of the GUI as displayed on the display device of the CAS system, wherein a surgical tool 120, such as an awl, a screwdriver, or the like, used in a surgery is displayed. The surgical tool 120 is tracked in space for its position and orientation by the CAS system. A representation of the tool 120 can then be displayed, overlaid on any one of the antero-posterior plane view 60, the sagittal plane view 61 and the non-imaged plane view 62. The display of the tool 120 may be useful for permitting a surgeon to follow the progress (position and orientation in time) of the surgery tool. The surgery tool 120 can be displayed along any preferred orthogonal view, or position and orientation information about the surgery tool 120 can be presented on one, two, or all the three views 60, 61, 62, as desired. This typically involves the scaling of the surgery tool 120 proportionally with the plane view(s) 60, 61, 62 on which it is displayed.

Figure 10:
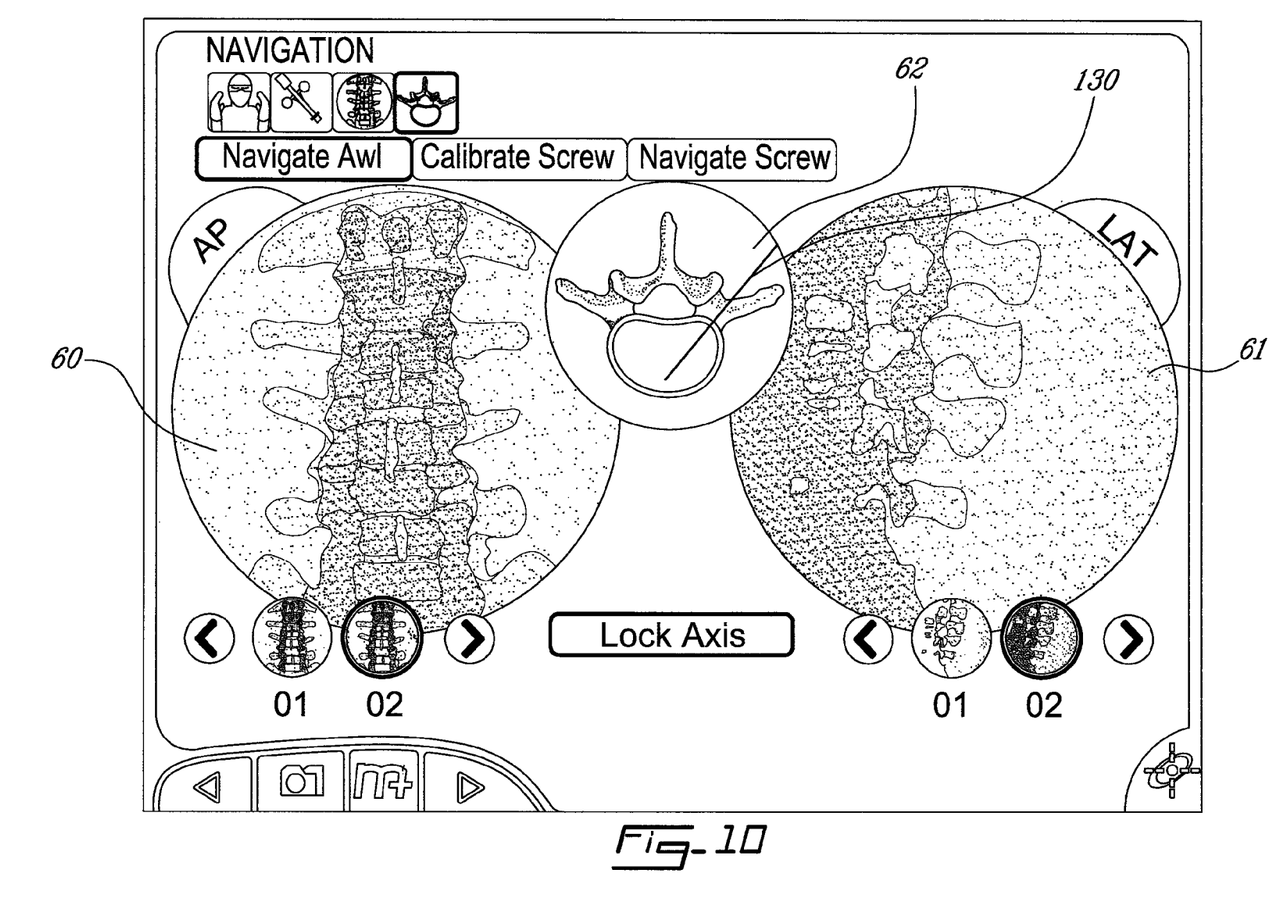
FIG. 10 is schematic illustrating a screenshot of the GUI of FIG. 4, wherein a locked guiding marker for a pedicular screw is shown on the axial plane view.

FIG. 10 shows a screenshot of the GUI as displayed on the display device of the CAS system, wherein a guiding marker 130 is displayed on the non-imaged view 62, as locked into position. The guiding marker 130 may in fact be displayed on any one(s) of the plane views 60, 61, 62. The guiding marker 130 is used as a guide by the user when moving a surgery tool with respect to the vertebra for inserting a device into the vertebra. In this illustrated case, the guiding marker 130 is used as a guide for inserting a screw in the pedicle of the vertebra. The guiding marker 130 is typically positioned by a user and locked into position on the display device. As a surgery tool or device is also displayed on the plane views, the user may validate the alignment of the tool or device relative to the marking guide 130. It is noted that a similar guiding marker may also be used to perform other types of operation on other types of objects.

Figure 11:
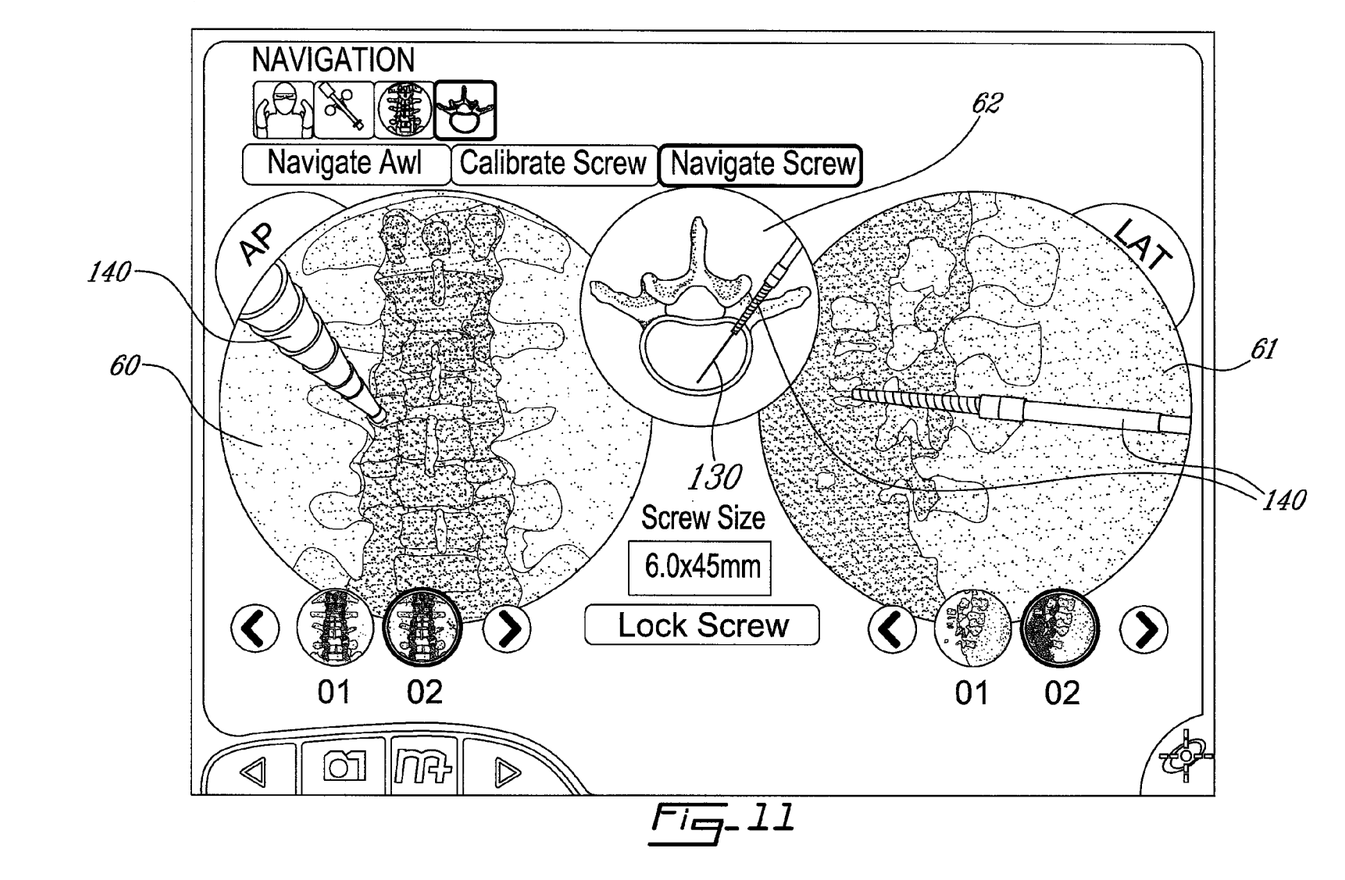
FIG. 11 is schematic illustrating a screenshot of the GUI of FIG. 4, wherein a screw is being inserted along the locked guiding marker.

FIG. 11 illustrates the navigation process wherein a screw 140 is inserted into the pedicle of a vertebra. The screw 140 is being inserted along the guiding marker 130 locked into position. In this case, the guiding marker 130 is displayed on the non-imaged or axial plane view 62 only and the screw 140 is displayed on one or more of the plane views 60, 61, and 62. This provides the user with multiple aspects from which to see the progress of the surgery. The user is being guided by the guiding marker 130 in the axial plane view 62 as the screw advances in the vertebra.

Figure 12:
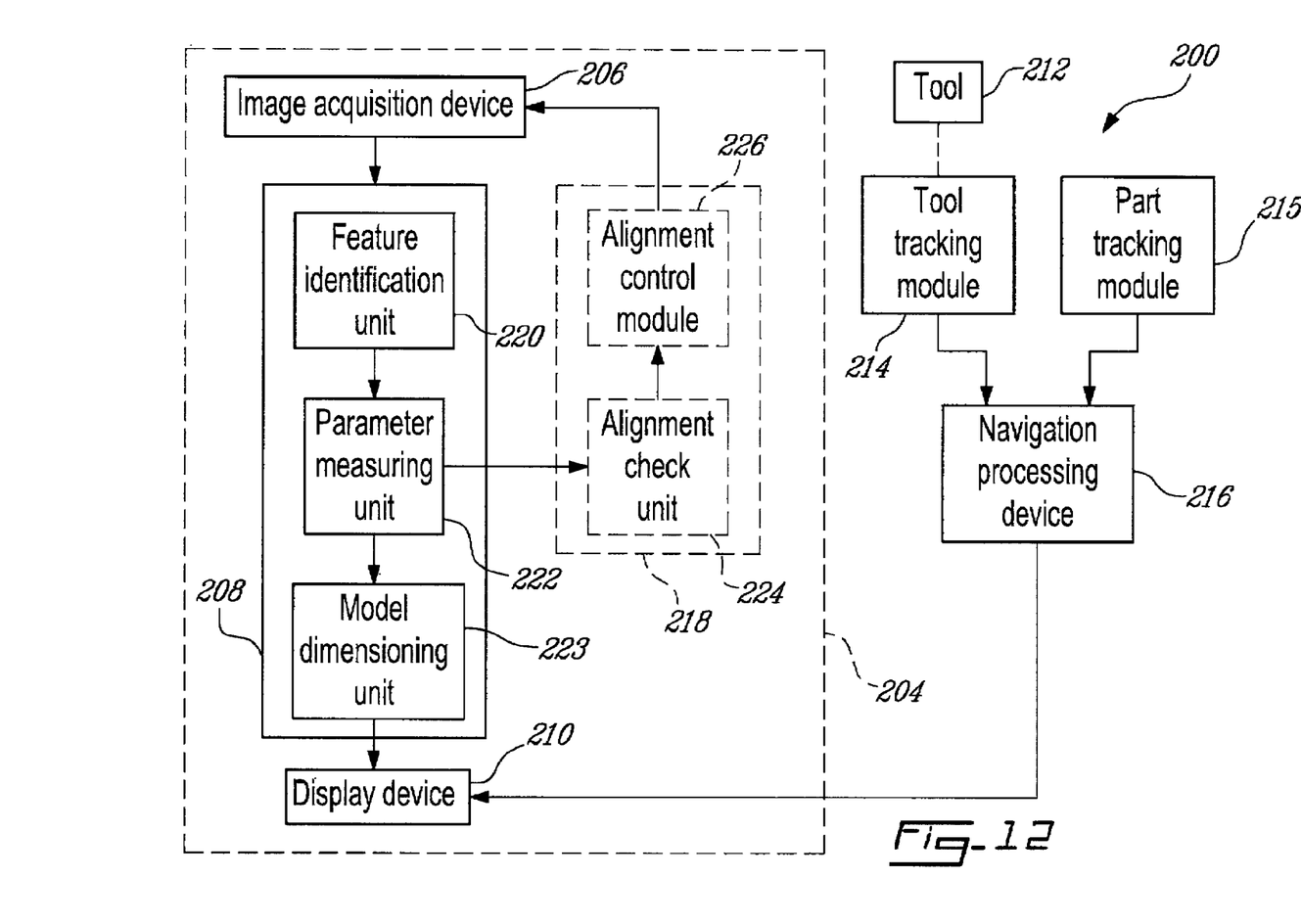
FIG. 12 is a block diagram of a computer-assisted surgery system having an imaging system generating a non-imaged plane view of an object, in accordance with an example embodiment.

FIG. 12 illustrates the Computer-Assisted Surgery (CAS) system 200. In this embodiment, the CAS system 200 has an imaging system 204 for generating a non-imaged plane view of an anatomical part. The imaging system 204 comprises an image acquisition device 206, an image processing device 208 and a display device 210. The CAS system 200 also makes use of one or more tools 212 with a tool tracking module 214 mounted thereon to track the position and orientation of the tool 212 in space or relative to the anatomical part as an operation, such as a surgery, is being conducted on the anatomical part. Tracking modules may also be mounted to other devices to be used in manipulating the anatomical part. Examples of tools used in surgery include an awl and implants or screws that are to be implanted in the anatomical part, such as a bone. The anatomical part may also have a part tracking module 215 installed thereon before the operation begins in order to also track a position and an orientation of the anatomical part in space. The CAS system 200 also has a navigation processing device 216 and an alignment device 218.

The image acquisition device 206 is a device permitting imaging of the anatomical part along a first plane view and a second plane view. In the specific case described herein, the image acquisition device 206 is a fluoroscope.

The imaged plane views captured by the image acquisition device 206 are transferred to the image processing device 208, where they are used to generate a non-imaged plane view. The image processing device 208 generates the non-imaged plane view according to the method described hereinabove with reference to FIG. 5. It has a feature identification unit 220, a parameter measuring unit 222 and a model dimensioning unit 223. The feature identification unit 220 identifies features of the anatomical part in the first plane view and the second plane view, according to the model of the anatomical part which defines the features and dimension parameters related to the features. The parameter measuring unit 222 measures values of the dimension parameters from the features identified by the feature identification unit 220. The model dimensioning unit 223 dimensions the model of the anatomical part with the dimension parameters adjusted to the values measured by the parameter measuring unit 222.

The display device 208 displays, in the non-imaged plane view on the GUI, the model of the anatomical part as dimensioned. The first and second plane views are also typically displayed on the GUI.

It will be understood that all safety measures are taken to ensure a proper referencing of the anatomical part and tool(s) 212 on the plane views displayed on the display device 210. Such a referencing is herein provided using the tool tracking module 214 and the part tracking module 215. Data tracked by the tool tracking module 214 and the part tracking module 215 is transferred to the navigation processing device 216 which generates a representation of the tool(s) 212 according to the position and orientation of the tool 212 relative to the anatomical part. The representation of the tool(s) 212 may be overlaid in register with the anatomical part on any one of the imaged and non-imaged plane views by the display device 210.

If an alignment is to be provided, the alignment device 218 has an alignment check unit 224 and an alignment control module 226. The alignment check unit 224 determines whether imaged plane views captured by the image acquisition device 206 are in alignment with their respective planes as described in reference with FIGS. 6B-6E and 7B-7C. As explained above, the alignment check unit 224 typically uses a combination of dimension parameters measured by the parameter measuring unit 222 to determine whether the imaged plane views are in proper alignment, according to predetermined conditions. Alternatively, the operator may determine that the imaged views are improper for misalignment. If the imaged plane views are not in proper alignment, the alignment control module 226 corrects the alignment by reorienting the plane views typically based on feedback provided by the measured dimension parameters, until the alignment check unit 224 determines that the alignment is correct, or until the operator is satisfied.

It will be understood that the embodiments described herein are intended to be illustrative only and that other embodiments are also contemplated.

For example, it is noted that the method and the system described herein may also applied to other types of computer-assisted surgeries. Any other type of bone, such as knee bones for example, may be modeled with features for generating a non-imaged plane view based on dimension parameters measured on imaged plane views.

While illustrated in the block diagrams as groups of discrete components communicating with each other via distinct data signal connections, it will be understood by those skilled in the art that the system is implemented from a combination of hardware and software components. Some components may be implemented by a given function or operation of a hardware or software system, and many of the data paths illustrated in FIG. 12 can be implemented by data communication within a computer application or an operating system. FIG. 12 is thus provided solely for illustrative purposes and it is understood that varying embodiments are contemplated.

The embodiment(s) of the invention described above is(are) intended to be exemplary only. The scope of the invention is therefore intended to be limited solely by the scope of the appended claims.

We claim:

1. A method for generating a display of a tracked surgical object relative to a non-imaged scaled general model in plane view of a vertebra in computer-assisted surgery, the method comprising:
receiving a general model of the vertebra comprising features and dimension parameters related to said features, the general model being non patient specific;
obtaining at least a first plane view of the anatomical part;
identifying said features in said at least first plane view;
measuring values of said dimension parameters from said features identified in said at least first plane view;
generating said non-imaged scaled general model in a transverse plane view of the vertebra by scaling said general model with said dimension parameters adjusted to said values;
tracking a surgical object relative to said vertebra while a user manipulates said surgical object in space; and
displaying on a display device of a computer-assisted surgery system by generating a representation of said surgical object to be overlaid in register on said transverse plane view of the vertebra, using the tracking of the surgical object.

2. The method as claimed in claim 1, further comprising obtaining a second plane view of the vertebra, said first plane view and second plane view being obtained along different orientations relative to said vertebra;
wherein said identifying said features comprises identifying said features in said first plane view and said second plane view; and
wherein said measuring values comprises measuring values of said dimension parameters from said features identified in said first plane view and said second plane view.

3. The method as claimed in claim 1, further comprising:
determining whether said first plane view is in alignment with a corresponding plane defined by the object; and
if said first plane view is not in alignment:
correcting the alignment; and
obtaining again said first plane view of the object with the corrected alignment.

4. The method as claimed in claim 2, wherein said first plane view is obtained along an antero-posterior plane of the vertebra and said second plane view is obtained along a sagittal plane of the vertebra.

5. The method as claimed in claim 1, wherein:
identifying said features comprises identifying a side vertebral body contour, a pedicle contour and a spinous process contour.

6. The method as claimed in claim 5, wherein measuring values comprises measuring a distance between said side vertebral body contour and said pedicle contour, and a distance between said spinous process contour and said pedicle contour.

7. The method as claimed in claim 2, wherein said generating comprises generating said first plane view, said second plane view and said non-imaged scaled general model in a same graphical user interface of the computer-assisted surgery system.

8. The method as claimed in claim 1, wherein said obtaining a first plane view comprises acquiring said first plane view using a fluoroscopic imaging device.

9. A computer-assisted surgery system for generating a display of a tracked surgical object relative to a non-imaged scaled general model in plane view of a vertebra for assisting a surgery, the system comprising:
an imaging acquisition device having a first axis for obtaining a first plane view of the vertebra;

an image generating device providing a non-imaged plane view of said vertebra comprising:
a feature identification unit for identifying features of said vertebra in at least said first plane view;
a parameter measuring unit for measuring values of dimension parameters from said features identified; and
a model dimensioning unit for dimensioning a general model of said vertebra with said measured values of dimension parameters to generate said non-imaged scaled general model in transverse plane view of the vertebra, the general model being non patient specific;
a display device for displaying said non-imaged scaled general model in said transverse plane view of the vertebra; and
a navigation processing device for generating a representation of a surgical object to be overlaid in register on at least said transverse plane view of the vertebra, using a tracking of said surgical object relative to said anatomical part, to provide visual feedback on at least said non-imaged scaled general model while said surgical object is manipulated.

10. The system as claimed in claim 9, wherein the imaging acquisition device has a second axis for obtaining a second plane view of the vertebra, said feature identification unit identifying features of said anatomical part in said first plane view and said second plane view and said parameter measuring unit measuring values of said dimension parameters from said features identified in said first plane view and in said second plane view.

11. The system as claimed in claim 10, wherein said first plane view is an antero-posterior plane view, said second plane view is a sagittal plane view.

12. The system as claimed in claim 9, further comprising:
an alignment check unit for determining whether said first plane view is in alignment with a corresponding plane defined by the vertebra; and
an alignment control module for correcting the alignment if said first plane view is not in alignment, by reorienting said imaging acquisition device to obtain said first plane view in alignment with said vertebra.

13. The system as claimed in claim 9, wherein said features comprise a side vertebral body contour, a pedicle contour and a spinous process contour.

14. The system as claimed in claim 13, wherein said dimension parameters comprise a distance between said side vertebral body contour and said pedicle contour, and a distance between said spinous process contour and said pedicle contour.

15. The system as claimed in claim 9, wherein said imaging acquisition device comprises a fluoroscopic imaging device.

16. The system as claimed in claim 9, wherein said display device displays at least said first plane view, and said transverse plane view of the vertebra simultaneously, and wherein said navigation processing device generates the representation of the surgical object overlaid on both the transverse plane view and the first plane view of the vertebra.

* * * * *